United States Patent
Nakashima et al.

(10) Patent No.: US 7,214,785 B2
(45) Date of Patent: May 8, 2007

(54) HUMAN-TYPE ANTI-BLOOD COAGULATION FACTOR VIII ANTIBODY

(75) Inventors: Toshihiro Nakashima, Kumamoto-ken (JP); Masato Yuguchi, Kumamoto-ken (JP)

(73) Assignee: Juridical Foundation The Chemo-Sero-Therapeutic Research Institute, Kumamoto-shi (JP)

( * ) Notice: Subject to any disclaimer, the term of this patent is extended or adjusted under 35 U.S.C. 154(b) by 327 days.

(21) Appl. No.: 10/344,514

(22) PCT Filed: Jun. 11, 2002

(86) PCT No.: PCT/JP02/05783

§ 371 (c)(1),
(2), (4) Date: Feb. 12, 2003

(87) PCT Pub. No.: WO02/101040

PCT Pub. Date: Dec. 19, 2002

(65) Prior Publication Data

US 2004/0120951 A1    Jun. 24, 2004

(30) Foreign Application Priority Data

Jun. 12, 2001   (JP) ............................ 2001-177640

(51) Int. Cl.
    C07H 21/04   (2006.01)
(52) U.S. Cl. .............. 536/23.53; 530/387.3; 530/388.25; 424/134.1; 424/135.1; 424/145.1
(58) Field of Classification Search ............ 536/23.53; 424/133.1, 135.1, 145.1; 530/387.3, 338.25
    See application file for complete search history.

(56) References Cited

U.S. PATENT DOCUMENTS 5,693,762 A * 12/1997 Queen et al. ............ 530/387.3

FOREIGN PATENT DOCUMENTS

| JP | 2838166 B2 | 10/1998 |
| WO | WO 01/04269 A1 | 1/2001 |
| WO | WO 01/62907 A1 | 8/2001 |

OTHER PUBLICATIONS

Gavilondo et al., "Antibody engineering at the millennium" (2000) Biotechniques, 29;128-145.*
Hu et al. "Minibody: A novel engineered anti-carcinoembryonic antigen antibody fragment (single-chain Fv-CH3) which exhibits rapid, high-level targeting of xenografts" (1996) Cancer Research, 56:3055-3061.*
Janeway et al., Immunobiology, Third edition, Garland Publishing Inc., (1997) 3:7-3.9).*
van den Brink, Edward et al., BLOOD, vol. 97, No. 4, pp. 966-972, (2001).
van den Brink, Edward N. et al., BLOOD, vol. 95, No. 2, pp. 558-563, (2000).
van den Brink, Edward N. et al., BLOOD, vol. 96, No. 2, pp. 540-545, (2000).
Victor, Kimberly D. et al., Eur. J. Immunol., vol. 22, pp. 2231 to 2236, (1992).
Marc G. Jacquemin et al.; BLOOD, vol. 92, No. 2, Jul. 15, 1998, pp. 496-506.
Marc Jacquemin et al.; Blood; Jan. 1, 2000, vol. 95, No. 1, pp. 156-163.
James D. Marks et al.; J. Mol. Biol., 1991, No. 222, pp. 581-597.
W.H. Ouehand et al.; The International Congress on Thrombosis and Hemostasis, Jun. 1995 (Israel) (1995, ISTH).
J. Davis et al.; The International Congress on Thrombosis and Hemostasis, Jun. 1997.
John F. Healey et al.; Blood, vol. 92, No. 10, Nov. 15, 1998, pp. 3701-3709.
F.R. Rosendaal et al.; British Journal of Haematology, 1990, No. 75, pp. 525-530.
Ted Koster et al.; The Lancet; vol. 345, Jan. 21, 1995, pp. 152-155.
Frits R. Rosendaal; Seminars in Hematology, vol. 34, No. 3, Jul. 1997, pp. 171-187.
Maura Mhic Iomhair et al.; Thrombosis Research, vol. 87, No. 4, pp. 359-362, 1997.

* cited by examiner

Primary Examiner—G. R. Ewoldt
Assistant Examiner—Michale Szperka
(74) Attorney, Agent, or Firm—Birch, Stewart, Kolasch & Birch, LLP (57) ABSTRACT

The present invention provides a human antibody against blood coagulation factor VIII (hereinafter also referred to as "FVIII") and an antibody fragment that binds to human FVIII and specifically inhibits the coagulation activity of human FVIII. ScFv display phage libraries, prepared by using scFv DNAs constructed by random combinations of immunoglobulin VH chain genes and VL chain genes from lymphocytes from hemophilia A patients, is reacted with FVIII immobilized to a solid phase via anti-FVIII monoclonal antibody, and scFv clones capable of binding to FVIII are cloned to reveal VH and VL chains of FVIII-specific antibody.

8 Claims, 3 Drawing Sheets

Fig. 1

FVIII Measurement by ELISA

SEQUENCE LISTING

```
<160> NUMBER OF SEQ ID NOS: 18

<210> SEQ ID NO 1
<211> LENGTH: 360
<212> TYPE: DNA
<213> ORGANISM: Homo sapiens

<400> SEQUENCE: 1
caggtgcagc tggtgcagtc tggggctgag gtgaagaagc ctggggcctc agtgaaggtc      60
tcctgcaagg tgtccggata caccctcact gaattatcca tccactgggt gcgacaggct     120
cctgaaaaag ggcttgagtg gataggaggt cttgatcgtg aagacgggaa aacagtctcc     180
gcacagaggt tccagggcag agtcaccatg accgaggaca cacccacaga cacaacctac     240
atgcaactga ccagcctgtc atctgaggac acggccgtgt attactgtgc aacaggtgtt     300
gcttccgatg acgatgcttt tgagatctgg ggccaaggga caacggtcac cgtctcttca     360

<210> SEQ ID NO 2
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 2 cag gtg cag ctg gtg cag tct ggg gct gag gtg aag aag cct ggg gcc       48
Gln Val Gln Leu Val Gln Ser Gly Ala Glu Val Lys Lys Pro Gly Ala
 1               5                  10                  15 tca gtg aag gtc tcc tgc aag gtg tcc gga tac acc ctc act gaa tta       96
Ser Val Lys Val Ser Cys Lys Val Ser Gly Tyr Thr Leu Thr Glu Leu
             20                  25                  30 tcc atc cac tgg gtg cga cag gct cct gaa aaa ggg ctt gag tgg ata      144
Ser Ile His Trp Val Arg Gln Ala Pro Glu Lys Gly Leu Glu Trp Ile
         35                  40                  45 gga ggt ctt gat cgt gaa gac ggg aaa aca gtc tcc gca cag agg ttc      192
Gly Gly Leu Asp Arg Glu Asp Gly Lys Thr Val Ser Ala Gln Arg Phe
     50                  55                  60 cag ggc aga gtc acc atg acc gag gac aca ccc aca gac aca acc tac      240
```

| | | | | | | | | | | | | | | | | |
|---|---|---|---|---|---|---|---|---|---|---|---|---|---|---|---|---|
| Gln | Gly | Arg | Val | Thr | Met | Thr | Glu | Asp | Thr | Pro | Thr | Asp | Thr | Thr | Tyr | |
| 65 | | | | 70 | | | | | 75 | | | | | 80 | | |

```
atg caa ctg acc agc ctg tca tct gag gac acg gcc gtg tat tac tgt    288
Met Gln Leu Thr Ser Leu Ser Ser Glu Asp Thr Ala Val Tyr Tyr Cys
             85                  90                  95 gca aca ggt gtt gct tcc gat gac gat gct ttt gag atc tgg ggc caa    336
Ala Thr Gly Val Ala Ser Asp Asp Asp Ala Phe Glu Ile Trp Gly Gln
            100                 105                 110 ggg aca acg gtc acc gtc tct tca                                    360
Gly Thr Thr Val Thr Val Ser Ser
            115                 120

<210> SEQ ID NO 3
<211> LENGTH: 324
<212> TYPE: DNA
<213> ORGANISM: Homo sapiens

<400> SEQUENCE: 3
gacatccagt tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa acgt                                           324

<210> SEQ ID NO 4
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 4 gac atc cag ttg acc cag tct cca tcc tcc ctg tct gca tct gta gga     48
Asp Ile Gln Leu Thr Gln Ser Pro Ser Ser Leu Ser Ala Ser Val Gly
  1               5                  10                  15 gac aga gtc acc atc act tgc cgg gca agt cag agc att agc agc tat     96
Asp Arg Val Thr Ile Thr Cys Arg Ala Ser Gln Ser Ile Ser Ser Tyr
             20                  25                  30 tta aat tgg tat cag cag aaa cca ggg aaa gcc cct aag ctc ctg atc    144
Leu Asn Trp Tyr Gln Gln Lys Pro Gly Lys Ala Pro Lys Leu Leu Ile
         35                  40                  45 tat gct gca tcc agt ttg caa agt ggg gtc cca tca agg ttc agt ggc    192
Tyr Ala Ala Ser Ser Leu Gln Ser Gly Val Pro Ser Arg Phe Ser Gly
     50                  55                  60 agt gga tct ggg aca gat ttc act ctc acc atc agc agt ctg caa cct    240
Ser Gly Ser Gly Thr Asp Phe Thr Leu Thr Ile Ser Ser Leu Gln Pro
 65                  70                  75                  80 gaa gat ttt gca act tac tac tgt caa cag agt tac agt acc ccg ctc    288
Glu Asp Phe Ala Thr Tyr Tyr Cys Gln Gln Ser Tyr Ser Thr Pro Leu
                 85                  90                  95 act ttc ggc gga ggg acc aag gtg gag atc aaa cgt                    324
Thr Phe Gly Gly Gly Thr Lys Val Glu Ile Lys Arg
            100                 105

<210> SEQ ID NO 5
<211> LENGTH: 360
<212> TYPE: DNA
<213> ORGANISM: Homo sapiens
```

-continued

<400> SEQUENCE: 5

| gaggtgcagc | tggtgcagtc | tggggttgag | gtgaagaagt | ctggggcctc | agtgaaggtc | 60 |
| tcctgcaagg | tgtccggata | caccctcact | gaattatcca | tccactgggt | gcgacaggct | 120 |
| cctgaaaaag | ggcttgagtg | gataggaggt | cttgatcgtg | aagacgggaa | agcagtctcc | 180 |
| gcacagaggt | tccagggcag | agtcaccatg | accgaggaca | catccacaga | cacaacctac | 240 |
| atgcaactga | ccagcctgtc | atctgaggac | acggccgtgt | attactgtgc | aacaggtgtt | 300 |
| gcttccgatg | acgatgcttt | tgaaatctgg | ggccaaggga | caatggtcac | cgtctcttca | 360 |

<210> SEQ ID NO 6
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 6

| gag | gtg | cag | ctg | gtg | cag | tct | ggg | gtt | gag | gtg | aag | aag | tct | ggg | gcc | 48 |
| Glu | Val | Gln | Leu | Val | Gln | Ser | Gly | Val | Glu | Val | Lys | Lys | Ser | Gly | Ala | |
| 1 | | | | 5 | | | | | 10 | | | | | 15 | | |

| tca | gtg | aag | gtc | tcc | tgc | aag | gtg | tcc | gga | tac | acc | ctc | act | gaa | tta | 96 |
| Ser | Val | Lys | Val | Ser | Cys | Lys | Val | Ser | Gly | Tyr | Thr | Leu | Thr | Glu | Leu | |
| | | | 20 | | | | | 25 | | | | | 30 | | | |

| tcc | atc | cac | tgg | gtg | cga | cag | gct | cct | gaa | aaa | ggg | ctt | gag | tgg | ata | 144 |
| Ser | Ile | His | Trp | Val | Arg | Gln | Ala | Pro | Glu | Lys | Gly | Leu | Glu | Trp | Ile | |
| | | 35 | | | | | 40 | | | | | 45 | | | | |

| gga | ggt | ctt | gat | cgt | gaa | gac | ggg | aaa | gca | gtc | tcc | gca | cag | agg | ttc | 192 |
| Gly | Gly | Leu | Asp | Arg | Glu | Asp | Gly | Lys | Ala | Val | Ser | Ala | Gln | Arg | Phe | |
| 50 | | | | | 55 | | | | | 60 | | | | | | |

| cag | ggc | aga | gtc | acc | atg | acc | gag | gac | aca | tcc | aca | gac | aca | acc | tac | 240 |
| Gln | Gly | Arg | Val | Thr | Met | Thr | Glu | Asp | Thr | Ser | Thr | Asp | Thr | Thr | Tyr | |
| 65 | | | | 70 | | | | | 75 | | | | | 80 | | |

| atg | caa | ctg | acc | agc | ctg | tca | tct | gag | gac | acg | gcc | gtg | tat | tac | tgt | 288 |
| Met | Gln | Leu | Thr | Ser | Leu | Ser | Ser | Glu | Asp | Thr | Ala | Val | Tyr | Tyr | Cys | |
| | | | 85 | | | | | 90 | | | | | 95 | | | |

| gca | aca | ggt | gtt | gct | tcc | gat | gac | gat | gct | ttt | gaa | atc | tgg | ggc | caa | 336 |
| Ala | Thr | Gly | Val | Ala | Ser | Asp | Asp | Asp | Ala | Phe | Glu | Ile | Trp | Gly | Gln | |
| | 100 | | | | | 105 | | | | | 110 | | | | | |

| ggg | aca | atg | gtc | acc | gtc | tct | tca | | | | | | | | | 360 |
| Gly | Thr | Met | Val | Thr | Val | Ser | Ser | | | | | | | | | |
| | 115 | | | | | 120 | | | | | | | | | | |

<210> SEQ ID NO 7
<211> LENGTH: 324
<212> TYPE: DNA
<213> ORGANISM: Homo sapiens

<400> SEQUENCE: 7

| gacatccagt | tgacccagtc | tccatcctcc | ctgtctgcat | ctgtaggaga | cagagtcacc | 60 |
| atcacttgcc | gggcaagtca | gagcattagc | agctatttaa | attggtatca | gcagaaacca | 120 |
| gggaaagccc | ctaagctcct | gatctatgct | gcatccagtt | tgcaaagtgg | ggtcccatca | 180 |
| aggttcagtg | gcagtggatc | tgggacagat | ttcactctca | ccatcagcag | tctgcaacct | 240 |
| gaagattttg | caacttacta | ctgtcaacag | agttacagta | ccccgatcac | cttcggccaa | 300 |
| gggacacgac | tggagattaa | acgt | | | | 324 |

<210> SEQ ID NO 8
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 8

| gac | atc | cag | ttg | acc | cag | tct | cca | tcc | tcc | ctg | tct | gca | tct | gta | gga | 48 |
| Asp | Ile | Gln | Leu | Thr | Gln | Ser | Pro | Ser | Ser | Leu | Ser | Ala | Ser | Val | Gly | |
| 1 | | | | 5 | | | | | 10 | | | | | 15 | | |

| gac | aga | gtc | acc | atc | act | tgc | cgg | gca | agt | cag | agc | att | agc | agc | tat | 96 |
| Asp | Arg | Val | Thr | Ile | Thr | Cys | Arg | Ala | Ser | Gln | Ser | Ile | Ser | Ser | Tyr | |
| | | | 20 | | | | | 25 | | | | | 30 | | | |

| tta | aat | tgg | tat | cag | cag | aaa | cca | ggg | aaa | gcc | cct | aag | ctc | ctg | atc | 144 |
| Leu | Asn | Trp | Tyr | Gln | Gln | Lys | Pro | Gly | Lys | Ala | Pro | Lys | Leu | Leu | Ile | |
| | | 35 | | | | | 40 | | | | | 45 | | | | |

| tat | gct | gca | tcc | agt | ttg | caa | agt | ggg | gtc | cca | tca | agg | ttc | agt | ggc | 192 |
| Tyr | Ala | Ala | Ser | Ser | Leu | Gln | Ser | Gly | Val | Pro | Ser | Arg | Phe | Ser | Gly | |
| | 50 | | | | | 55 | | | | | 60 | | | | | |

| agt | gga | tct | ggg | aca | gat | ttc | act | ctc | acc | atc | agc | agt | ctg | caa | cct | 240 |
| Ser | Gly | Ser | Gly | Thr | Asp | Phe | Thr | Leu | Thr | Ile | Ser | Ser | Leu | Gln | Pro | |
| 65 | | | | | 70 | | | | | 75 | | | | | 80 | |

| gaa | gat | ttt | gca | act | tac | tac | tgt | caa | cag | agt | tac | agt | acc | ccg | atc | 288 |
| Glu | Asp | Phe | Ala | Thr | Tyr | Tyr | Cys | Gln | Gln | Ser | Tyr | Ser | Thr | Pro | Ile | |
| | | | | 85 | | | | | 90 | | | | | 95 | | |

| acc | ttc | ggc | caa | ggg | aca | cga | ctg | gag | att | aaa | cgt | | | | | 324 |
| Thr | Phe | Gly | Gln | Gly | Thr | Arg | Leu | Glu | Ile | Lys | Arg | | | | | |
| | | | 100 | | | | | 105 | | | | | | | | |

<210> SEQ ID NO 9
<211> LENGTH: 360
<212> TYPE: DNA
<213> ORGANISM: Homo sapiens

<400> SEQUENCE: 9

| caggtgcagc tggtgcagtc tggggttgag gtgaagaagc ctggggcctc agtgaaggtc | 60 |
| tcctgcaagg tgtccggata caccctcact gaattatcca tccactgggt gcgacaggct | 120 |
| cctgaaaaag ggcttgagtg gataggaggt cttgatcgtg aagacgggaa aacagtctcc | 180 |
| gcacagaggt tccagggcag agtcaccatg accgaggaca catccacaga cacaacctac | 240 |
| atgcaactga ccagcctgtc atctgaggac acggccgtgt attactgtgc aacaggtgtt | 300 |
| gcttccgatg acgatgcttt tgaaatctgg ggccaaggga ccacggtcac cgtctcctca | 360 |

<210> SEQ ID NO 10
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 10

| cag | gtg | cag | ctg | gtg | cag | tct | ggg | gtt | gag | gtg | aag | aag | cct | ggg | gcc | 48 |
| Gln | Val | Gln | Leu | Val | Gln | Ser | Gly | Val | Glu | Val | Lys | Lys | Pro | Gly | Ala | |
| 1 | | | | 5 | | | | | 10 | | | | | 15 | | |

| tca | gtg | aag | gtc | tcc | tgc | aag | gtg | tcc | gga | tac | acc | ctc | act | gaa | tta | 96 |
| Ser | Val | Lys | Val | Ser | Cys | Lys | Val | Ser | Gly | Tyr | Thr | Leu | Thr | Glu | Leu | |
| | | | 20 | | | | | 25 | | | | | 30 | | | |

| tcc | atc | cac | tgg | gtg | cga | cag | gct | cct | gaa | aaa | ggg | ctt | gag | tgg | ata | 144 |
| Ser | Ile | His | Trp | Val | Arg | Gln | Ala | Pro | Glu | Lys | Gly | Leu | Glu | Trp | Ile | |

-continued

```
              35                  40                  45
gga ggt ctt gat cgt gaa gac ggg aaa aca gtc tcc gca cag agg ttc      192
Gly Gly Leu Asp Arg Glu Asp Gly Lys Thr Val Ser Ala Gln Arg Phe
     50                  55                  60 cag ggc aga gtc acc atg acc gag gac aca tcc aca gac aca acc tac      240
Gln Gly Arg Val Thr Met Thr Glu Asp Thr Ser Thr Asp Thr Thr Tyr
 65                  70                  75                  80 atg caa ctg acc agc ctg tca tct gag gac acg gcc gtg tat tac tgt      288
Met Gln Leu Thr Ser Leu Ser Ser Glu Asp Thr Ala Val Tyr Tyr Cys
                 85                  90                  95 gca aca ggt gtt gct tcc gat gac gat gct ttt gaa atc tgg ggc caa      336
Ala Thr Gly Val Ala Ser Asp Asp Asp Ala Phe Glu Ile Trp Gly Gln
            100                 105                 110 ggg acc acg gtc acc gtc tcc tca                                      360
Gly Thr Thr Val Thr Val Ser Ser
        115                 120

<210> SEQ ID NO 11
<211> LENGTH: 324
<212> TYPE: DNA
<213> ORGANISM: Homo sapiens

<400> SEQUENCE: 11
gacatcgtga tgacccagtc tccatcctcc ctgtctgcat ctgtaggaga cagagtcacc     60
atcacatgcc gggcaagtca gtccattacc agatatttaa attggtatca gcagaaacca    120
gggaaagccc ctaaactcct gatctttgct gcatccagtt tgcaaagtgg ggtcccatca    180
cggttcagtg gcagtggatc tgggacagaa ttcactctca ccatcagcag tctgcaacct    240
gaggattttg cgacttacta ctgtcaacac agttacacta ccccgctcac tttcggcgga    300
gggaccaaag tggatatcaa acgt                                           324

<210> SEQ ID NO 12
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 12 gac atc gtg atg acc cag tct cca tcc tcc ctg tct gca tct gta gga       48
Asp Ile Val Met Thr Gln Ser Pro Ser Ser Leu Ser Ala Ser Val Gly
  1               5                  10                  15 gac aga gtc acc atc aca tgc cgg gca agt cag tcc att acc aga tat       96
Asp Arg Val Thr Ile Thr Cys Arg Ala Ser Gln Ser Ile Thr Arg Tyr
                 20                  25                  30 tta aat tgg tat cag cag aaa cca ggg aaa gcc cct aaa ctc ctg atc      144
Leu Asn Trp Tyr Gln Gln Lys Pro Gly Lys Ala Pro Lys Leu Leu Ile
             35                  40                  45 ttt gct gca tcc agt ttg caa agt ggg gtc cca tca cgg ttc agt ggc      192
Phe Ala Ala Ser Ser Leu Gln Ser Gly Val Pro Ser Arg Phe Ser Gly
         50                  55                  60 agt gga tct ggg aca gaa ttc act ctc acc atc agc agt ctg caa cct      240
Ser Gly Ser Gly Thr Glu Phe Thr Leu Thr Ile Ser Ser Leu Gln Pro
 65                  70                  75                  80 gag gat ttt gcg act tac tac tgt caa cac agt tac act acc ccg ctc      288
Glu Asp Phe Ala Thr Tyr Tyr Cys Gln His Ser Tyr Thr Thr Pro Leu
                 85                  90                  95 act ttc ggc gga ggg acc aaa gtg gat atc aaa cgt                      324
Thr Phe Gly Gly Gly Thr Lys Val Asp Ile Lys Arg
            100                 105
```

```
                            100                 105

<210> SEQ ID NO 13
<211> LENGTH: 5
<212> TYPE: PRT
<213> ORGANISM: Homo sapiens
<220> FEATURE:
<223> OTHER INFORMATION: CDR1 of SEQUENCE No. 2, 6 or 10

<400> SEQUENCE: 13

Glu Leu Ser Ile His
                5

<210> SEQ ID NO 14
<211> LENGTH: 17
<212> TYPE: PRT
<213> ORGANISM: Homo sapiens
<220> FEATURE:
<223> OTHER INFORMATION: CDR2 of SEQUENCE No. 2, 6 or 10
<220> FEATURE:
<221> NAME/KEY: Unsure
<222> LOCATION: (9)..(9)
<223> OTHER INFORMATION: Xaa represents Thr or Ala.
<220> FEATURE:
<221> NAME/KEY: misc_feature
<222> LOCATION: (9)..(9)
<223> OTHER INFORMATION: Xaa represents Thr or Ala.

<400> SEQUENCE: 14

Gly Leu Asp Arg Glu Asp Gly Lys Xaa Val Ser Ala Gln Arg Phe Gln
 1               5                  10                  15

Gly

<210> SEQ ID NO 15
<211> LENGTH: 11
<212> TYPE: PRT
<213> ORGANISM: Homo sapiens
<220> FEATURE:
<223> OTHER INFORMATION: CDR3 of SEQUENCE No. 2, 6 or 10

<400> SEQUENCE: 15

Gly Val Ala Ser Asp Asp Asp Ala Phe Glu Ile
 1               5                  10

<210> SEQ ID NO 16
<211> LENGTH: 11
<212> TYPE: PRT
<213> ORGANISM: Homo sapiens
<220> FEATURE:
<223> OTHER INFORMATION: CDR1 of SEQUENCE No. 4, 8 or 12
<220> FEATURE:
<221> NAME/KEY: Unsure
<222> LOCATION: (7)..(7)
<223> OTHER INFORMATION: Xaa represents Ser or Thr.
<220> FEATURE:
<221> NAME/KEY: misc_feature
<222> LOCATION: (7)..(7)
<223> OTHER INFORMATION: Xaa represents Ser or Thr.
<220> FEATURE:
<221> NAME/KEY: Unsure
<222> LOCATION: (8)..(8)
<223> OTHER INFORMATION: Xaa represents Ser or Arg.
<220> FEATURE:
<221> NAME/KEY: misc_feature
<222> LOCATION: (8)..(8)
<223> OTHER INFORMATION: Xaa represents Ser or Arg.

<400> SEQUENCE: 16

Arg Ala Ser Gln Ser Ile Xaa Xaa Tyr Leu Asn
 1               5                  10
```

```
<210> SEQ ID NO 17
<211> LENGTH: 7
<212> TYPE: PRT
<213> ORGANISM: Homo sapiens
<220> FEATURE:
<223> OTHER INFORMATION: CDR2 of SEQUENCE No. 4, 8 or 12

<400> SEQUENCE: 17

Ala Ala Ser Ser Leu Gln Ser
 1               5

<210> SEQ ID NO 18
<211> LENGTH: 9
<212> TYPE: PRT
<213> ORGANISM: Homo sapiens
<220> FEATURE:
<223> OTHER INFORMATION: CDR3 of SEQUENCE No. 4, 8 or 12
<220> FEATURE:
<221> NAME/KEY: Unsure
<222> LOCATION: (2)..(2)
<223> OTHER INFORMATION: Xaa represents Gln or His.
<220> FEATURE:
<221> NAME/KEY: misc_feature
<222> LOCATION: (2)..(2)
<223> OTHER INFORMATION: Xaa represents Gln or His.
<220> FEATURE:
<221> NAME/KEY: Unsure
<222> LOCATION: (5)..(5)
<223> OTHER INFORMATION: Xaa represents Ser or Thr.
<220> FEATURE:
<221> NAME/KEY: misc_feature
<222> LOCATION: (5)..(5)
<223> OTHER INFORMATION: Xaa represents Ser or Thr.
<220> FEATURE:
<221> NAME/KEY: Unsure
<222> LOCATION: (8)..(8)
<223> OTHER INFORMATION: Xaa represents Leu or Ile.
<220> FEATURE:
<221> NAME/KEY: misc_feature
<222> LOCATION: (8..(8)
<223> OTHER INFORMATION: Xaa represents Leu or Ile.

<400> SEQUENCE: 18

Gln Xaa Ser Tyr Xaa Thr Pro Xaa Thr
 1               5
```

HUMAN-TYPE ANTI-BLOOD COAGULATION FACTOR VIII ANTIBODY

This application is the national phase under 35 U.S.C. § 371 of PCT International Application No. PCT/JP02/05783 which has an International filing date of Jun. 11, 2002, which designated the United States of America.

TECHNICAL FIELD OF THE INVENTION

The present invention relates to a provision of a human inhibitor antibody against blood coagulation factor VIII (hereinafter also referred to as "FVIII") and an antibody fragment that bind to human FVIII and thereby specifically inhibits the coagulating activity of FVIII.

BACKGROUND OF THE INVENTION

Hemophilia A is a genetic disease where disorder or deficiency of FVIII leads to reduction of the blood coagulation activity, resulting in bleeding in the bowels or at the joint, etc. For treatment of patients suffering from hemophilia A, supplemental treatment of FVIII has been carried out. In about 10% (8 to 15%) out of the patients who received supplemental treatment, however, induction of an antibody to FVIII has been observed. This antibody, called "anti-FVIII inhibitor antibody", makes supplemental treatment with the blood coagulation factors ineffective and hemostatic management of the hemophilia patients extremely difficult.

Elucidation of nature of the anti-FVIII inhibitor antibody and its production mechanism would enable inhibiting or regulating production of the inhibitor antibody. Up till the present, there has been research using an anti-FVIII inhibitor antibody (polyclonal antibody) purified from the sera of hemophilia patients having anti-FVIII inhibitor antibodies or a mouse anti-FVIII inhibitor antibody (mouse monoclonal antibody) to thereby provide much information. As to cloning of anti-FVIII inhibitor antibody from patients, however, there has almost been no report.

On the other hand, epidemiological study has shown that hemophilia patients exhibited low occurrence of arteriosclerosis such as myocardial infarction, in particular, significantly low occurrence of lethal myocardial infarction (Br. J. Haemotol. 1990, 75, 525–530; Lancet 1995, 345(8943) 152–155); and that an increased FVIII level in plasma may possibly be a risk factor for arterial infarction or arteriosclerosis (Semin. Hematol. 1997, 34, 171–187; Thromb. Res. 1997, 84, 359–362).

Thus, it is expected that, if lowered blood coagulation could be maintained by using an anti-FVIII inhibitor antibody, this would contribute to prevention and treatment of arterial infarction and arteriosclerosis. In particular, an anti-FVIII antibody that specifically recognizes activated FVIII free from von Willebrand factor (hereinafter also referred to as "vWF") exhibits much long clearance in blood as failing to complex with FVIII usually bound with vWF in blood, and hence can be an excellent anti-thrombotic drug in which lowered blood coagulation may be maintained for a long period of time with a single administration and bleeding or other adverse side effects can be much reduced.

There have already been numerous attempts to prepare mouse monoclonal antibodies to FVIII in many laboratories including those prepared by the present inventors and so a number of monoclonal antibodies to FVIII have been produced. Some of them have been proved to inhibit the FVIII activity and to behave as an anti-FVIII inhibitor antibody. With these mouse monoclonal antibodies, numerous results have been obtained including analysis of regions that inhibit the FVIII activity, etc.

A completely human anti-FVIII inhibitor antibody, however, has scarcely been prepared with success although it has been attempted over more than ten years in many laboratories with the hybridoma technique (human/mouse or human/human hybridoma technique) or the EB transformation technique, using lymphocytes from patients having anti-FVIII inhibitor antibodies.

In 1998, Marc G. Jacquemin et al. reported first establishment of the method for preparing a completely human anti-Factor VIII inhibitor antibody using the EB transformation technique (Blood, 92(2), 1998, 496–506). They established BO2C11 antibody which was thought to inhibit binding of FVIII with vWF or with phospholipids and to recognize the C2 domain of FVIII. VH and VL genes of this antibody were derived from DP5 fragment and Vκ3, respectively. They also succeeded in establishment of clones producing anti-Factor VIII inhibitor antibodies to the C1 domain with the similar method and reported that the antibodies are derived from DP64 and Vκ3 (Blood, 95, 2000, 156–163). Up till the present, it is only Marc G. Jacquemin et al. who has ever established a clone producing such a human-derived anti-FVIII inhibitor antibody with the hybridoma technique (human/mouse or human/human hybridoma technique) or the EB transformation technique.

On the other hand, the antibody display phage technology reported by J. D. Marks et al. (J. Mol. Biol, 222, 581–597, 1991) is advantageous in that an antibody repertoire from lymphocytes from patients can be screened in a shorter period of time and in more clones than the conventional hybridoma technique or the EB transformation technique. In recent years, there has been an attempt to use this antibody display phage technology for isolating the inhibitor antibody.

W. H. Ouehand et al. reported in the International Congress on Thrombosis and Hemostasis, 1995, June (Israel) (1995, ISTH) that they cloned a human anti-FVIII single-chain antibody (scFv) from human antibody display phage libraries from healthy donors and a library of synthetic human phage antibodies. J. Davis et al. also reported in the International Congress on Thrombosis and Hemostasis, 1997, June that they cloned a human anti-FVIII single-chain antibody (scfv) from human antibody display phage libraries wherein VH genes were derived from hemophilia patients and VL genes were from healthy donors. In these reports, however, the human antibody display phage libraries were constructed in a synthetic or semi-synthetic manner in which not both of VH and VL was derived from hemophilia patients. Moreover, although the clones obtained in these reports bound to FVIII as shown by ELISA, it was not proved whether the clones inhibited the coagulation activity of FVIII.

In 2000, E. N. van den Brink et al. reported that they constructed an antibody display phage library in which VL chain genes were derived from healthy donors and VH chain genes were from patients having the inhibitor antibodies and isolated four clones reactive with FVIII, of which two clones were reactive with the C2 domain of FVIII whereas the other two were reactive with the A2 domain of FVIII [van Den Brink, Human antibodies with specificity for the C2 domain of factor VIII are derived from VH1 germline genes (Blood, 2000; 95: 558–563); Molecular analysis of human anti-factor VIII antibodies by V gene phage display identifies a new epitope in the acidic region following the A2 domain (Blood, 2000; 96: 540–545)].

It has been reported that the C2 domain of FVIII was involved in binding with vWF or with phospholipids and was a principal recognition region of many anti-FVIII inhibitor antibodies present in blood from patients (Healey, J. F. et al., Residues Glu2181-Val2243 contain a major determinant of the inhibitory epitope in the C2 domain of human factor VIII, Blood, 1998, 92, 3701–3709).

According to the study by van den Brink et al., the antibody fragments to the C2 domain obtained thereby did not have an inhibitor activity to FVIII. Accordingly, a human anti-FVIII antibody with the inhibitor activity has not yet successfully been isolated, hence failing to provide sufficient information.

The reason why a human anti-FVIII antibody with the inhibitor activity could not successfully be isolated with the antibody display phage technology was presumed to be that genes of VL chain of antibody fragments were not derived from patients and that there might be some problems in the screening procedure.

DISCLOSURE OF THE INVENTION

The present inventors addressed and dissolved the problems mentioned above. As a result, the present inventors succeeded in isolating novel anti-FVIII inhibitor antibodies distinctly having specificity and the inhibitor activity to FVIII from lymphocytes of a patient by the antibody display phage technology and analyzed the VH and VL chains of said specific antibodies.

BEST MODE FOR CARRYING OUT THE INVENTION

In order to obtain information about the variable (V) region of a human anti-FVIII inhibitor antibody, the present inventors first amplified the immunoglobulin heavy and light chains cDNAs from peripheral blood B lymphocytes of a hemophilia A patient having anti-FVIII inhibitor antibodies by RT-PCR. Both of the obtained cDNAs were linked together with linker DNAs to prepare single-chain Fv (scFv) DNAs in random combinations of VH and VL chains from patient lymphocytes.

The scFv DNAs were incorporated into phagemid vector pCANTAB5E to prepare scFv display phage libraries from hemophilia A patients comprising $10^7$ clones. The libraries were then reacted with FVIII immobilized to a solid phase via anti-FVIII monoclonal antibody to screen anti-FVIII scFv display phage clones capable of binding with FVIII.

The anti-FVIII monoclonal antibody used herein is prepared by the conventional techniques and includes a mouse monoclonal antibody. The anti-FVIII monoclonal antibody preferably recognizes a conformational epitope of the A2 domain of FVIII or of an L chain of activated FVIII. With the use of such an antibody, it becomes possible to retain FVIII on the solid support without significantly affecting its conformation. Thus, in this screening system, phage clones shall be obtained which display anti-FVIII scFvs that recognize epitopes other than those recognized by respective mouse anti-FVIII monoclonal antibodies.

By labeling the monoclonal antibody with biotin and using avidin-immobilized magnetic particles as a solid phase, anti-FVIII scFv display phage clones capable of binding with human FVIII may easily be recovered.

Biotin-conjugated mouse anti-FVIII monoclonal antibody allows for screening without need of purified FVIII and with a trace amount of FVIII.

As a result of screening, seven scFv clones having the activity to bind to anti-FVIII were isolated and three out of these clones inhibited the coagulation activity of FVIII. The obtained three clones consisted of a VH gene from DP-5 (1–24) of VH1 family and a VL gene from DPK9(012/02) of Vκ1 family. The other four clones consisted of a VH gene from either DP-88 or 4M28 of VH1 family and a VL gene from DPK22, Vg, DPK9 or IGLV6S1, which were different from those of the clones having the inhibitor activity. VH genes of the clones that inhibited the coagulation activity of FVIII were derived from the DP-5 segment as in Marc G. Jacquemin et al. but an amino acid sequence of CDR3 in VH differed greatly from that in Marc G. Jacquemin et al. Also, observing that the activity to bind to FVIII of these clones was almost lost after mutation of serine or threonine in CDR3 in the VL chain into glutamine, we revealed that CDR3 in the VL chain plays an important role in binding of these clones to FVIII.

The nucleotide and amino acid sequences of the VH and VL chains of the obtained three clones (YK3.3.38, YK3.3.40 and YK3.3.50) are shown in sequence listing in which the sequences of the VH and VL chains of YK3.3.38 were shown in SEQ ID NOs: 1-2 and 3-4; the sequences of the VH and VL chains of YK3.3.40 in SEQ ID NOs: 5-6 and 7-8; and the sequences of the VH and VL chains of YK3.3.50 in SEQ ID NOs: 9-10 and 11-12, respectively.

Among these sequences, the amino acid sequences of CDR1 to CDR3 in the VH and VL chains are shown in SEQ ID NOs: 13 to 18. CDR1, CDR2 and CDR3 are as defined by E. A. Kabat et al. [Sequences of Proteins of Immunological Interest, 4th ed., U.S. Department of Health and Human Services, Washington D.C. (1987)].

[VH Chain]
CDR1: Glu Leu Ser Ile His (SEQ ID NO: 13)
CDR2: Gly Leu Asp Arg Glu Asp Gly Lys Xaa Val Ser Ala Gln Arg Phe Gln Gly (Xaa=Thr or Ala) (SEQ ID NO: 14)
CDR3: Gly Val Ala Ser Asp Asp Asp Ala Phe Glu Ile (SEQ ID NO: 15)

[VL Chain]
CDR1: Arg Ala Ser Gln Ser Ile Xa1 Xa2 Tyr Leu Asn (Xa1=Ser or Thr; Xa2=Ser or Arg) (SEQ ID NO: 16)
CDR2: Ala Ala Ser Ser Leu Gln Ser (SEQ ID NO: 17)
CDR3: Gln Xa1 Ser Tyr Xa2 Thr Pro Xa3 Thr (Xa1=Gln or His; Xa2=Ser or Thr; Xa3=Leu or Ile) (SEQ ID NO: 18)

The nucleotide and amino acid sequences shown in SEQ ID NOs: 1-2 and 3-4, 5-6 and 7-8, 9-10 and 11-12 correspond respectively to the V region heavy chain (VH chain) and light chain (VL chain) of the human anti-FVIII inhibitor antibody having the activity to inhibit the coagulation activity of FVIII.

The VH chain and/or the VL chain disclosed herein were obtained in the form of scFv by the antibody display phage technology. However, its application is not limited to scFv.

Namely, the VH chain and/or the VL chain disclosed herein may also be in the form of a complete molecule of an antibody in which the VH chain and/or the VL chain are linked to the constant region of a human immunoglobulin, or in the form of other antibody fragments, including Fab, Fab' or F(ab')$_2$ in which the VH chain and/or the VL chain are linked to a portion of the constant region of a human immunoglobulin, or a single-chain antibody (scAb) in which scFv is linked to the constant region of a human immunoglobulin.

The present invention also envisages a modified protein molecule in which a protein molecule of the antibody or the antibody fragment mentioned above is conjugated with a high molecular weight modifier.

As a result of analysis of nature of the antibody fragment obtained according to the present invention, the epitope of FVIII recognized by the antibody fragment was lost by SDS treatment of FVIII. Besides, upon binding with the antibody fragment, FVIII could not bind to phospholipids or vWF. It was thus concluded that the antibody fragment did not bind to FVIII bound with vWF as in blood flow but binds only to an activated form of FVIII free from vWF.

The antibody fragment competes with inhibitor antibodies from plasma of a patient. It was thus presumed that the antibody fragment recognized the same epitope as that recognized by the patient inhibitor antibodies, a structure dependent epitope in the C2 domain, and had the similar property to that of the patient inhibitor antibodies.

The inhibitor activity to FVIII of the antibody fragment was extremely potent, i.e. 6,700 to 29,100 Bethesda unit/mg.

As mentioned above, the human monoclonal antibody and antibody fragment molecule of the present invention can potently inhibit the coagulation activity of FVIII and hence may be used as a medicament for prevention and treatment of thrombosis. In particular, the human monoclonal antibody and antibody fragment molecule of the present invention does not recognize a FVIII-VWF complex but instead recognizes only an activated form of FVIII free from von Willebrand factor, which allows for reaction with the activated FVIII alone but not with the FVIII-vWF complex as usually occurring in blood.

This demonstrates that the human monoclonal antibody and antibody fragment molecule of the present invention is an excellent novel anti-thrombotic agent in which excellent effects not found in the conventional anti-thrombotic agents may be expected such as a very long half-life in blood and less degree of adverse side effects such as bleeding and its effects may be monitored by APTT measurement.

Also, the human monoclonal antibody and antibody fragment molecule of the present invention, based on its property, may be combined with an anti-FVIII antibody recognizing a different epitope (antigen determinant) to provide an immunoassay for measuring a blood level of an activated FVIII free from vWF.

Moreover, the human monoclonal antibody and antibody fragment molecule of the present invention has many applications when formed into a complex with an immunosorbent material comprising an immunologically inactive adsorbent.

First, it can be applied for purifying a trace amount of FVIII present in human plasma or serum by affinity chromatography. It may also be applied for purifying FVIII produced in culture supernatant by transformed culture cells by the genetic recombination technique.

Secondly, the human monoclonal antibody and antibody fragment molecule of the present invention may be used in immunoassay for purifying anti-idiotype antibodies to the variable region of the molecule from human plasma or serum or human immunoglobulin fractions or preparations. This implies new options for treatment of patients having the inhibitor antibodies with similar property to that of the antibody of the present invention.

Namely, it is possible to inhibit the activity of the anti-FVIII inhibitor antibodies by removing the inhibitor antibodies by successively administering the anti-idiotype antibodies mentioned above to patients prior to or simultaneously with administration of the FVIII preparations or by immunoadsorbent technique using the idiotype antibodies. Currently, in treatment of patients having the inhibitor antibodies, especially in case of serious bleeding or during operation, a large amount of the FVIII preparations has been administered to the patients in order to neutralize the inhibitor antibodies in blood and to achieve hemostatic level. It is known, however, that this treatment induces increase in the inhibitor antibodies to lead to reduction of the hemostatic effect or tendency of bleeding. The anti-idiotype antibodies, on the contrary, are advantageous in that they have a low immunogenicity as a human antibody and less adverse side effects due to their specificity.

It also becomes possible to specifically remove inhibitor antibodies when a column is immobilized with the anti-idiotype antibodies in place of a column immobilized with Protein A that has been used for removal of inhibitor antibodies.

The present invention also provides a novel tolerance therapy drug for inducing production of anti-idiotype antibodies to the inhibitor antibody by using a peptide of the variable region, especially of the complementarity determining region (CDR), of the human monoclonal antibody or the antibody fragment of the present invention, or a high molecular weight carrier modified with said peptide. Tolerance therapy has already been attempted to patients having the inhibitor antibodies with the FVIII preparations. In this therapy, the FVIII preparations are repeatedly administered in a regular course to patients when no bleeding is seen so that an inhibitor titer is lowered or the inhibitor antibodies are wholly removed. This therapy however is disadvantageous in that it is extremely costly, it bears a risk of increased tendency of bleeding or anaphylaxis, and it can only be applied to patients who have the inhibitor antibodies at a comparatively lower level, because in this therapy the FVIII preparations at 100 to 200 units/kg are daily administered twice a day or the FVIII preparations at 25 units/kg are administered every other day over a long period of time.

Japanese patent No. 2838166 discloses a pharmaceutical composition for inhibition of inhibitor production using a immunological complex comprising an FVIII antigen and an FVIII inhibitor obtained from patient plasma and a method for inhibition of inhibitor production. However, the anti-FVIII inhibitor antibody used therein is basically prepared from human plasma components of patients and hence prodigious labor would be needed for preparing the component and homogeneity of quality could hardly be maintained. Moreover, cases were reported wherein a large number of immunological complexes were seen in plasma of patients who have the inhibitor antibodies. Therefore, enhanced deposition of the complexes in the spleen as well as adverse side effects need be considered.

In contrast, in accordance with the present invention, production of anti-idiotype antibodies to the inhibitor antibody is induced by using a peptide of the variable region, especially of the complementarity determining region (CDR), of the human monoclonal antibody or the antibody fragment of the present invention, or a high molecular weight carrier modified with said peptide, which would thus allow handling like the conventional vaccination.

When patients have the inhibitor antibodies with the same specificity and reactivity as those of the human monoclonal antibody and antibody fragment of the present invention, their idiotype is also thought to be the same.

The present inventors have found that, among the antibody variable regions disclosed herein, the CDR3 region of the H chain and the CDR3 region of the C chain particularly contribute stability in binding between the inhibitor antibodies and FVIII. Thus, it is expected that the action of the inhibitor antibodies in blood can be suppressed by immunizing patients with peptides of these CDRs to induce production of anti-idiotype antibodies. Besides, the method of the present invention, in which production of anti-idiotype antibodies to the complementarity determining region, among other things, of the inhibitor antibodies is induced, would enable a safe therapy of thrombosis which therapy is extremely specific and free from risk of increased tendency of bleeding, etc.

The human monoclonal antibody of the present invention can neutralize the coagulation activity of Factor VIII and be used as a medicament for prevention and treatment of thrombosis. In particular, the human monoclonal antibody of the present invention does not recognize a Factor VIII/von Willebrand factor complex but recognizes alone Factor VIII free from von Willebrand factor. Accordingly, it can be an excellent novel anti-thrombotic agent with an extremely long half-life in blood with less tendency of bleeding, the effect of which can be monitored by APTT measurement.

The human monoclonal antibody of the present invention also allows for detection of activated FVIII in blood.

The human monoclonal antibody of the present invention also enables isolation of a peptide to be an antigenic epitope and isolation of anti-idiotype antibodies in plasma. The obtained peptide and anti-idiotype antibodies are expected to be efficacious, from viewpoint of neutralization or tolerance mechanism, for treatment of hemophilia patients having the inhibitor antibody.

The present invention further provides a novel tolerance therapy drug for inducing production of anti-idiotype antibodies to the inhibitor antibodies by using a peptide of the variable region, especially of the complementarity determining region (CDR), of the human monoclonal antibody or the antibody fragment of the present invention, or a high molecular weight carrier modified with said peptide.

The present invention is explained in more detail by means of the following examples which are however not intended to restrict a scope of the present invention in any sense.

EXAMPLE 1

Construction of Phage Library from Hemophilia Patient:

A phage library was constructed with reference to the method reported by J. D. Marks et al. (J. Mol. Biol., 222: 581–597, 1991).

Lymphocytes were separated with Ficoll from peripheral blood (28 ml) from a patient having the anti-FVIII inhibitor antibody, washed thoroughly with PBS, and treated with ISOGEN (Nippon Gene Co., Ltd.) to prepare a total RNA. The obtained total RNA was divided into three portions, each of which was reverse-transcribed with p primers specific for the constant regions of human IgG, κ chain or λ chain with First Strand cDNA Synthesis Kit (Pharmacia bio tec) to prepare cDNAs for respective constant regions. The obtained cDNAs were then used as a template for amplifying antibody V region genes by polymerase chain reaction (PCR) using primers specific for gene families as a combination of VH+JH, Vκ+Jκ, and Vλ+Jλ, as reported by Marks et al.

VH genes and Vκ genes, and VH genes and Vλ genes, respectively, were linked together with linker DNAs by the assembly PCR technique to prepare single-chain scFv DNAs. The obtained scFv DNAs were added with NotI and SfiI restriction enzyme sites by PCR, electrophoresed on agarose gel and purified. The purified scFv DNAs were digested with restriction enzymes SfiI (Takara) and NotI (Takara) and cloned into phagemid pCANTAB5E (Pharmacia). The phagemids pCANTAB5E in which the scFv DNAs were incorporated were introduced into E. coli TG1 cells by electroporation separately for VH-Vκ and VH-Vλ. Judging from the number of TG1 cells transformed, it was estimated that VH-Vκ and VH-Vλ had diversity of $1.03 \times 10^7$ and $4.85 \times 10^6$ clones, respectively. Using the transformed TG1 cells, phage antibodies were expressed using M13KO7 helper phage to prepare a scFv display phage library derived from a patient.

EXAMPLE 2

Screening:

Factor VIII (Cross Eight M; 10 units/mL) dissolved in a screening buffer (4% skim milk, 0.5% bovine serum albumin, 50 μg/mL mouse IgG, 0.1% Tween 20, TBS; 500 μL) and either 0.5 μg/mL of anti-Factor VIII monoclonal antibodies conjugated with biotin FVIII:C14-182 (mouse; recognizing Factor VIII L chain) or FVIII:C14-282 (mouse; recognizing FVIII H chain A2 domain) dissolved in a screening buffer (500 μL) were mixed in a plastic tube (FALCON 2058) to react at room temperature for 30 minutes. Thereto was added the phage library displaying human antibody derived from patients (a solution of phage displaying single-chain antibodies; 1 mL) to react at room temperature for 1 hour and then at 4° C. overnight.

Avidin bound magnetic particles (Perseptive; 100 μL) treated with 2% skim milk/0.05% Tween 20/TBS were added to the above mixture of anti-FVIII monoclonal antibody conjugated with biotin/FVIII (1 mL) and the mixture was gently mixed upside-down for 15 minutes. The magnetic particles were collected with a magnetic rack and washed with 0.05% Tween 20/TBS eight times and then with Tris buffer twice. The magnetic particles after washing were suspended in a glycine buffer (1 mL) and the suspension was left to stand at room temperature for 10 minutes to elute the phage displaying single-chain antibodies. To the solution of eluted phage, after adjustment of pH with Tris (hydroxymethyl)aminomethane-HCl (pH 7.5; 500 μL), was added E. coli TG1 culture (5 mL) at logarithmic growth phase and the mixture was gently shaken at 37° C. for 1 hour to infect E. coli TG1.

The infected TG1 cells were centrifuged at 3,000×g for 5 minutes, and after removing supernatant, suspended in 2×YT medium (200 μL), inoculated on SOBAG plate, and cultured in an incubator at 30° C. overnight. The formed colonies were recovered by adding an appropriate amount of 2×YT medium and suspending the colonies with a scraper (Coastor). The TG1 cells (500 μL) were inoculated to 2×YTAG medium and rescued with a helper phage to prepare a human antibody display phage library after screening. Screening was repeated three times for each of the phage libraries derived from a hemophilia patient, VH-Vκ and VH-Vλ. After the third screening, clones were optionally selected from the SOBAG plate, and confirmation of scFv expression, confirmation of their specificity by FVIII sandwich ELISA and analysis of nucleotide sequence were made.

EXAMPLE 3

Expression and Recovery of scFv:

A soluble scFv was expressed with *E. coli* HB2151, recovered from *E. coli* periplasmic fraction and crudely purified. Affinity purification was performed with RAPAS Purification Module (Pharmacia Biotech) when further purification was needed.

Purity of the purified scFv protein was confirmed by SDS-polyacrylamide gel electrophoresis and Western blotting targeted to E-Tag epitope at the C-terminal of the scFv protein. A protein concentration of the purified scFv protein was determined with Protein Assay kit (BIO-RAD).

EXAMPLE 4

FVIII ELISA for Screening:

ELISA for screening the isolated clones was performed as described below.

Two anti-FVIII mouse monoclonal antibodies that recognize different antigen determinants, FVIII:C14-182 recognizing FVIII L chain and FVIII:C14-282 recognizing the A2 domain of FVIII H chain, were immobilized to an ELISA plate for screening. The anti-FVIII monoclonal antibodies (5 µg/mL; 100 µL/well), FVIII:C14-182 or FVIII:C14-282, were placed in an ELISA plate (MAXISORP module (Nunc)) and the plate was sealed with a plate sealer (Sanko Junyaku Co., Ltd.) and left to stand at room temperature or at 4° C. overnight to immobilize the antibodies. After washing with TBS three times, 1% BSA in TBS (300 µL/well) was added to the plate, which was then left to stand at room temperature for 1 hour for blocking.

To the ELISA plate was added a solution of Factor VIII (Cross Eight M1000; the Japanese Red Cross Society; 10 units/mL; 100 µL/well) and the plate was sealed with a plate sealer and left to stand at 37° C. for 2 hours. After the FVIII solution was discarded and the ELISA plate was washed five times with an ELISA plate washing solution, sample solutions (100 µL/well) containing either scFv or scFv display phage was added to react at room temperature overnight. After the sample solutions were discarded and the ELISA plate was washed five times with a washing solution, a secondary antibody labeled with horseradish peroxidase (100 µL/well) was added to react at 37° C. for 1 hour. After the reaction solution was discarded and the ELISA plate was washed five times with an ELISA plate washing solution, a substrate solution for development (TMBZ-hydrogen peroxide; 100 pL/well) was added to develop at room temperature to 37° C. for 5 to 10 minutes while the light was shielded. 1N Sulfuric acid (100 µL/well) was added to the plate to quench the development and an absorbance at 450 nm was measured with Molecular Device Multiplate Autoreader SPECTRA MAX. As a result, all the 99 clones estimated were confirmed to be specific to FVIII by FVIII sandwich ELISA.

EXAMPLE 5

Sequence Analysis of Clones:

The flanking regions of scFv gene of the isolated colonies were amplified by PCR. The obtained PCR products were digested with three to five restriction enzymes such as PstI and KpnI and electrophoresed on agarose gel and the colonies were classified based on their band patterns. As a result, 13 clones containing a complete scFv gene were identified. DNA sequences of VH genes and VL genes of these clones were determined with Dye Terminator Cycle Sequencing FS Ready Reaction Kit (Applied Biosystems).

EXAMPLR 6

Estimation of Isolated Human Anti-Factor VIII Single-chain Antibody:

FVIII ELISA and a coagulation activity inhibition test were performed for the purified scFvs to confirm that seven scFvs bound specifically to FVIII. Among these, three scFvs were found to inhibit the coagulation activity of EVIII. These three clones, YK3.3.38, YK3.3.40 and YK3.3.50, were further studied.

To a plate (MAXISORP module (Nunc)) immobilized with the anti-FVIII monoclonal antibodies, FVIII:C14-182 or FVIII:C14-282, was added a solution of EVIII (Cross Eight M1000; The Japanese Red Cross Society; 100 µL/well), prepared at 0.001 to 10 units/mL, and the ELISA plate was sealed with a plate sealer and left to stand at 37° C. for 2 hours. After the FVIII solution was removed by aspiration and the plate was washed five times with a washing solution, a solution of scFv (100 µL/well) was added to react at room temperature overnight. After the sample solution was removed by aspiration and the plate was washed five times with a washing solution, an anti-Etag antibody labeled with horseradish peroxidase (100 µL/well) was added to react at 37° C. for 1 hour. After the sample solution was removed by aspiration and the plate was washed five times with a washing solution, a substrate solution for development (TMBZ-hydrogen peroxide; 100 µL/well) was added to develop at room temperature to 37° C. for 10 minutes while the light was shielded. 1N Sulfuric acid (100 µL/well) was added to the plate to quench the development and an absorbance at 450 nm was measured with Molecular Device Multiplate Autoreader SPECTRA MAX.

Figure 1:
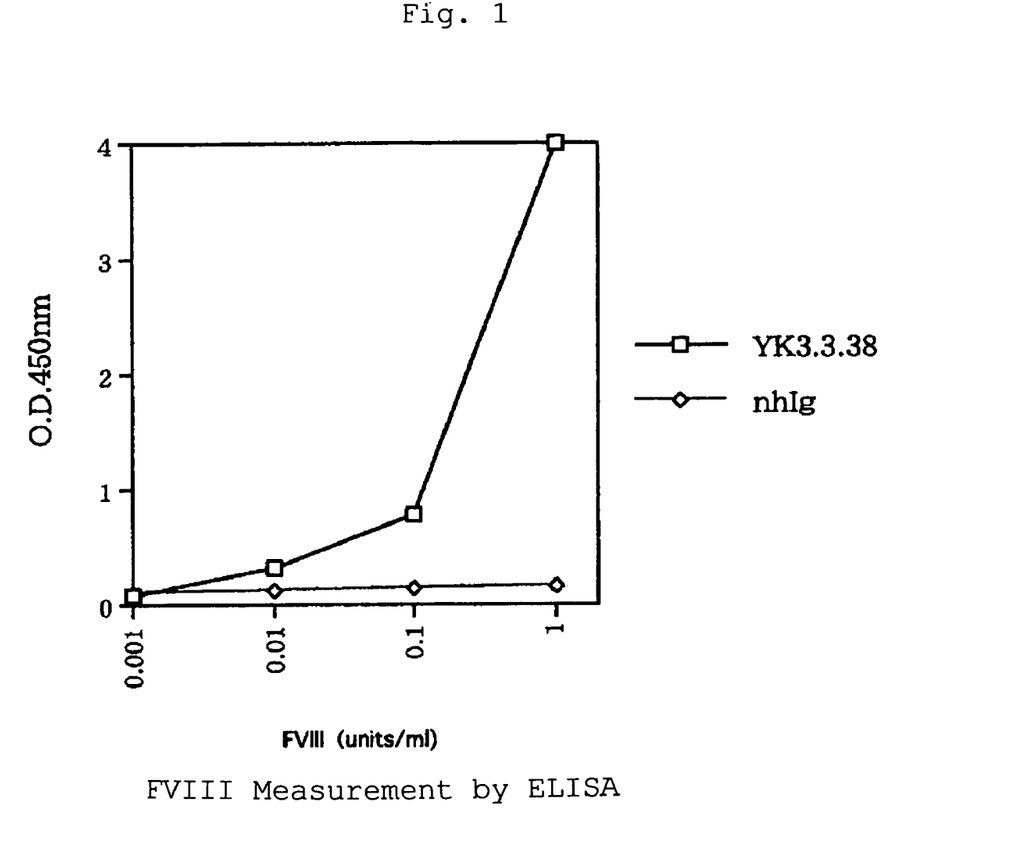
FIG. 1 shows a measurement of human FVIII by ELISA in which an ELISA plate immobilized with the anti-human FVIII A2 mouse monoclonal antibody is combined with the obtained scFv clones.

FIG. 1 shows the results obtained with YK3.3.38 scFv, indicating that FVIII could be detected and measured with a sensitivity of as high as 0.01 unit/ml or more. This measurement system had a sufficient sensitivity for monitoring the activated FVIII in blood since FVIII blood level has been reported to be 0.01 unit/ml or more even under circumstances with high tendency of bleeding.

EXAMPLE7

Coagulation Activity Inhibition Test:

The isolated human anti-Factor VIII single-chain antibodies were estimated by measuring Activated Partial Thromboplastin Time (APTT) using TestTeam FVIII kit (Daiichi Pure Chemicals Co., Ltd.) and FVIII deficient plasma (DADE).

The reaction on TestTeam FVIII kit was carried out in accordance with the attached manufacturer's instructions for the procedure (A), Endpoint method, except that a scale was reduced to ¼ for enabling measurement with a 96-well microtiter well.

Measurement of Activated Partial Thromboplastin Time (APTT) was performed with Fibrintimer (Behring) as described in: National Committee for Clinical Laboratory Standards. Collection, transport and processing of blood specimens for coagulation testing and performance of coagulation assays, 2nd Edition, Approved Guideline, NCCLS Publication H21-A2, Villanova, Pa. 1991; Sirridge, M. S.; Shannon, R., Laboratory Evaluation of Hemostasis and Thrombosis, 3rd Ed., Philadelphia: Lea and Febinger, 1983: 130–133.

For an antigen-antibody reaction, an equivalent amount of a dilution of the antibody sample and a solution of FVIII (Cross Eight M; 1 unit/ml) were mixed together to react at 37° C. for more than 2 hours. Measurement of TestTeam FVIII kit or Activated Partial Thromboplastin Time (APTT) was then performed.

Figure 2:
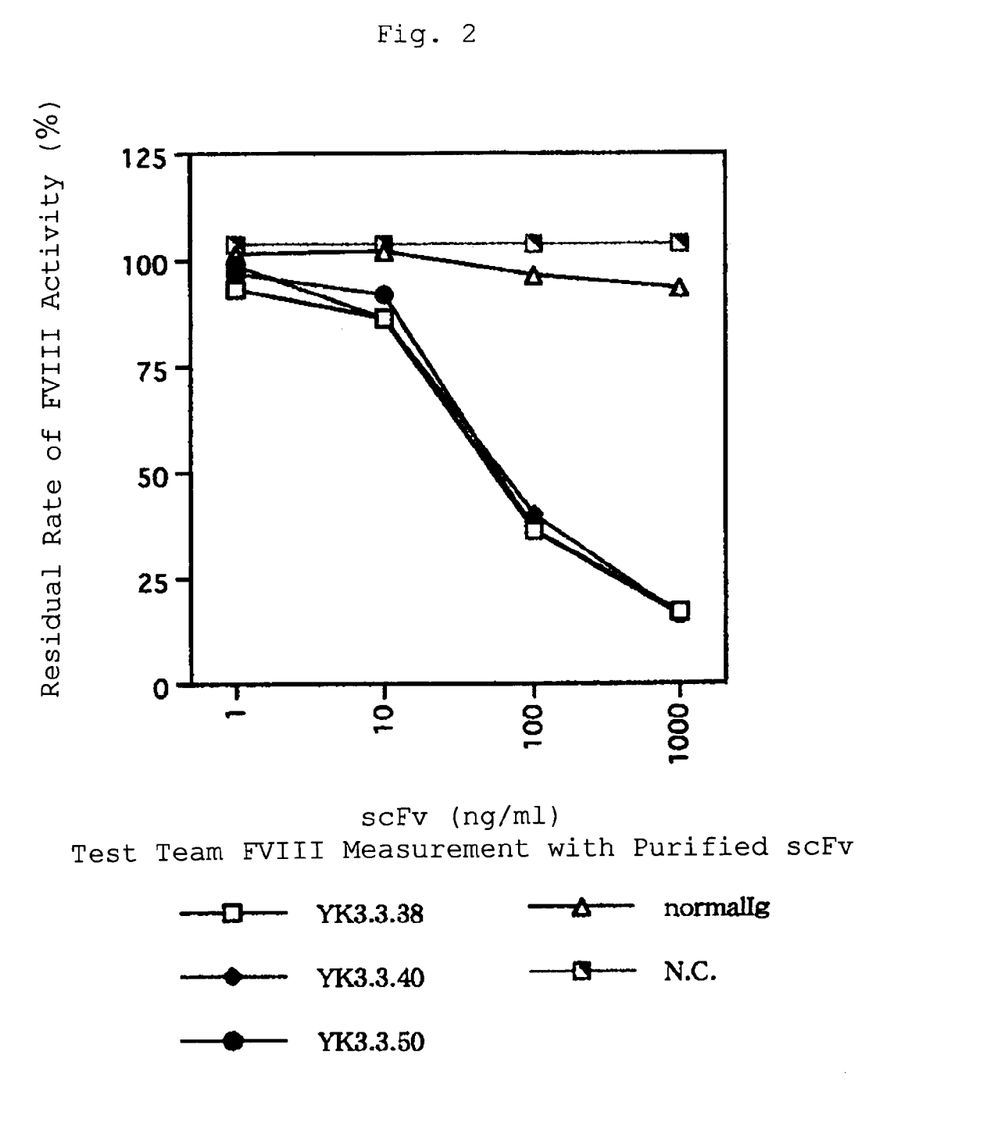
FIG. 2 shows a measurement of FVIII with TestTeam FVIII kit using the three purified anti-human FVIII scFvs.

FIG. 2 shows the results obtained with TestTeam FVIII kit, indicating that all the clones could potently inhibit the FVIII activity at a concentration of 10 ng/ml or more. Similar results were obtained with Activated Partial Thromboplastin Time (APTT).

EXAMPLE 8

Figure 3:
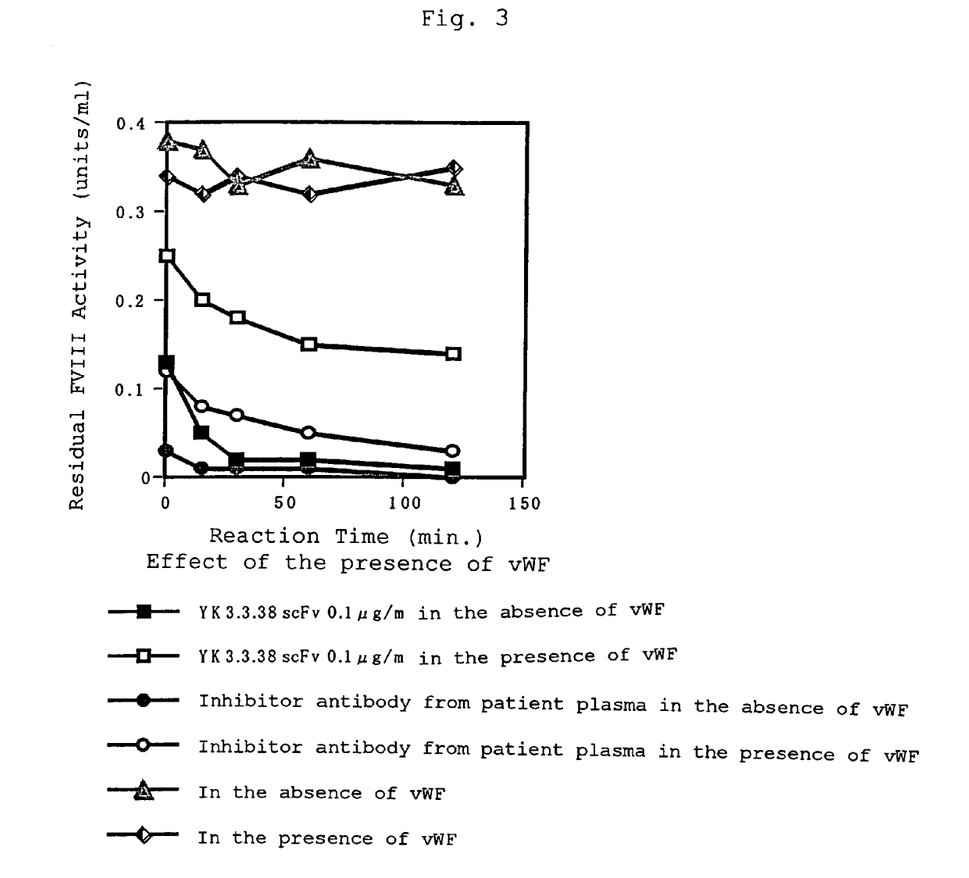
FIG. 3 shows estimation of a residual FVIII activity with the purified scFvs by measuring Activated Partial Thromboplastin Time (APTT) in which FVIII free from vWF or an FVIII preparation comprising multimeric vWF was used as human FVIII.

Study of Effect of the Presence of Von Willebrand Factor:

Effect of the presence of vWF was studied by using both FVIII almost free from vWF (Cross Eight M, the Japanese Red Cross Society) and purified FVIII comprising multimeric vWF (Confact F; Juridical Foundation the Chemo-Sero-Therapeutic Research Institute). FIG. 3 shows the results of measurement of Activated Partial Thromboplastin Time (APTT) obtained with YK3.3.38. For comparison, commercially available plasma from patients having the inhibitor antibodies (GedrgeKingMedical, Inc. lot. GK1833-929J2) was used.

The study revealed that the anti-FVIII antibody clones of the present invention, YK3.3.38, YK3.3.40 and YK3.3.50, did not inactivate FVIII bound with vWF but inactivated FVIII free from vWF.

The invention claimed is:

1. A single-chain Fv (scFv) polynucleotide comprising a sequence coding for a VH chain of a human antibody against blood coagulation factor VIII (FVIII) said human antibody against FVIII having an activity to inhibit the coagulation activity of human FVIII, linked to a sequence coding for a VL chain of the human antibody against FVIII, wherein said human antibody against FVIII specifically binds FVIII when FVIII is not bound to or in a complex with von Willebrand Factor (vWF), and wherein complementarity determining regions (CDR1 to CDR3) of said VH chain consist of the following amino acid sequences:

CDR1: Glu Leu Ser Ile His (SEQ ID NO: 13);

CDR2: Gly Leu Asp Arg Glu Asp Gly Lys Xaa Val Ser Ala Gln Mg Phe Gln Gly (Xaa=Thr or Ala) (SEQ ID NO: 14); and CDR3: Gly Val Ala Ser Asp Asp Asp Ala Phe Glu Ile (SEQ ID NO: 15), and wherein complementarity determining regions (CDR1 to CDR3) of said VL chain consist of the following amino acid sequences:

CDR1: Arg Ala Ser Gln Ser Ile Xa1 Xa2 Tyr Leu Asn (Xa1=Ser or Thr: Xa2=Ser or Arg) (SEQ ID NO: 16);

CDR2: Ala Ala Ser Ser Leu Gln Ser (SEQ ID NO: 17); and

CDR3: Gln Xa1 Ser Tyr Xa2 Thr Pro Xa3 Thr (Xa1=Gln or His; Xa2=Ser or Thr; Xa3=Leu or Ile) (SEQ ID NO: 18).

2. The scFv polynucleotide of claim 1 wherein said sequence coding for said VH chain consists of a nucleotide sequence coding for the amino acid sequence selected from the group consisting of SEQ ID NOs: 2, 6 and 10, and wherein said sequence coding for said VL chain consists of a nucleotide sequence coding for the amino acid sequence selected from the group consisting of SEQ ID NOs: 4, 8 and 12.

3. A polynucleotide coding for a human antibody fragment against FVIII comprising the single-chain Fv polynucleotide as set forth in claim 2 linked to either a sequence coding for a human antibody CH chain or a portion thereof or a sequence coding for a human antibody CL chain or a portion thereof.

4. A polynucleotide coding for human antibody against FVIII comprising a sequence coding for a VH chain of a human antibody against FVIII, said human antibody against FVIII having an activity to inhibit the coagulation activity of human FVIII, and a sequence coding for a VL chain of the human antibody against FVIII, wherein said human antibody against FVIII specifically binds FVIII when FVIII is not bound to or in a complex with von Willebrand Factor (vWF), and wherein said sequence coding for the VH chain and said sequence coding for the VL chain are bound to a sequence coding for a human antibody CH chain and a sequence coding for a human antibody CL chain respectively, and wherein complementarity determining regions (CDR1 to CDR3) of said VH chain consist of the following amino acid sequences:

CDR1: Glu Leu Ser Ile His (SEQ ID NO: 13);
CDR2: Gly Leu Asp Mg Glu Asp Gly Lys Xaa Val Ser Ala Gln Mg Phe Gln Gly (Xaa=Thr or Ala) (SEQ ID NO: 14); and
CDR3: Giy Val Ala Ser Asp Asp Asp Ala Phe Glu Ile (SEQ ID NO:15), and wherein complementarity determining regions (CDR1 to CDR3) of said VL chain consist of the following amino acid sequences:

CDR1: Arg Ala Ser Gln Ser Ile Xa1 Xa2 Tyr Leu Asn (Xa1=Ser or Thr; Xa2 Ser or Arg) (SEQ ID NO: 16);
CDR2:Ala Ala Ser Ser Leu Gln Ser (SEQ ID NO: 17); and
CDR3:Gln Xa1 Ser Tyr Xa2 Thr Pro Xa3 Thr (Xa1=Gln or His; Xa2=Ser or Thr; Xa3=Leu or Ile) (SEQ ID NO: 18).

5. The polynucleotide of claim 4 wherein said sequence coding for said VH chain consists of consist of a nucleotide sequence coding for the amino acid sequence selected from the group consisting of SEQ ID NOs: 2, 6 and 10, and wherein said sequence coding for said VL chain consists of a nucleotide sequence coding for the amino acid sequence selected from the group consisting of SEQ ID NOs: 4, 8 and 12.

6. A polynucleotide coding for human antibody against FVIII or an antigen binding fragment thereof comprising a sequence coding for a VH chain of a human antibody against FVIII, said human antibody against EVIII having an activity to inhibit the coagulation activity of human FVIII, and a sequence coding for a VL chain of the human antibody against FVIII, wherein said human antibody against FVIII specifically binds FVIII when FVIII is not bound to or in a complex with von Willebrand Factor (vWF), and wherein said sequence coding for the VH chain and said sequence coding for the VL chain are bound to a sequence coding for a human antibody CH chain or a portion thereof and a sequence coding for a human antibody CL chain or a portion thereof, respectively, and wherein complementarity determining regions (CDR1 to CDR3) of said VH chain consist of the following amino acid sequences:

CDR1: Glu Leu Ser Ile His (SEQ ID NO: 13);
CDR2: Gly Leu Asp Arg Glu Asp Gly Lys Xaa Val Ser Ala Gln Arg Phe Gln Gly (Xaa=Thr or Ala) (SEQ ID NO: 14); and
CDR3: Gly Val Ala Ser Asp Asp Asp Ala Phe Glu Ile (SEQ ID NO: 15), and wherein complementarity determining regions (CDR1 to CDR3) of said VL chain consist of the following amino acid sequences:

CDR1: Arg Ala Ser Gln Ser Ile Xa1 Xa2 Tyr Leu Asn (Xa1=Ser or Thr; Xa2=Ser or Arg) (SEQ ID NO: 16);
CDR2: Ala Ala Ser Ser Leu Gln Ser (SEQ ID NO: 17); and
CDR3: Gln Xa1 Ser Tyr Xa2 Thr Pro Xa3 Thr (Xa1=Gln or His; Xa2=Ser or Thr; Xa3=Leu or Ile) (SEQ ID NO: 18).

7. The polynucleotide of claim 6 wherein said sequence coding for said VH chain consists of a nucleotide sequence coding for the amino acid sequence selected from the group consisting of SEQ ID NOs: 2, 6 and 10, and wherein said sequence coding for said VL chain consists of a nucleotide sequence coding for the amino acid sequence selected from the group consisting of SEQ ID NOs: 4, 8 and 12.

8. The polynucleotide of claim 7 wherein said antibody fragment is selected from the group consisting of Fab, Fab' and F(ab')$_2$.

* * * * *